US00PP35297P3

(12) United States Plant Patent
Ruter

(10) Patent No.: US PP35,297 P3
(45) Date of Patent: Aug. 8, 2023

(54) ***THUJA* PLANT NAMED 'RUTTHU4'**

(50) Latin Name: *Thuja occidentalis*
Varietal Denomination: RutThu4

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/854,214

(22) Filed: Jun. 30, 2022

(65) Prior Publication Data

US 2023/0007822 P1 Jan. 5, 2023

Related U.S. Application Data

(60) Provisional application No. 63/217,004, filed on Jun. 30, 2021.

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

(56) References Cited

PUBLICATIONS

Canadian Food Inspection Agency for Thuja RutThu4 retrieved on Sep. 26, 2022 at https://inspection.canada.ca/english/plaveg/pbrpov/cropreport/ced/app00012409e.shtml, 2 pp. (Year: 2022).*
First Editions Shrub & Trees retrieved on Sep. 26, 2022 at https://firsteditionsplants.com/product/planet-earth-arborvitae/, 6 pp. (Year: 2022).*
Trademark Electronic Search System (TESS) retrieved on Sep. 26, 2022 at https://tmsearch.uspto.gov/bin/showfield?f=doc&state=4805: y4j5v6.3.28, 2 pp. (Year: 2022).*
License Agreement dated Mar. 30, 2020 (financial and personal information redacted), 7 pp. Jan. 10, 2023.

* cited by examiner

*Primary Examiner* — June Hwu
(74) *Attorney, Agent, or Firm* — ThomasHorstemeyer, LLP

(57) ABSTRACT

A new and distinct cultivar of *Thuja* plant named 'RutThu4', characterized by its compact, globose growth, similar in shape but larger in size and with a faster growth rate than some other *Thuja occidentalis* cultivars. 'RutThu4' also has disease resistance when grown in USDA Zone 8a, and has demonstrated both heat tolerance as well as cold hardiness to about −34° F. in trials conducted in Minnesota.

2 Drawing Sheets

Figure 1:
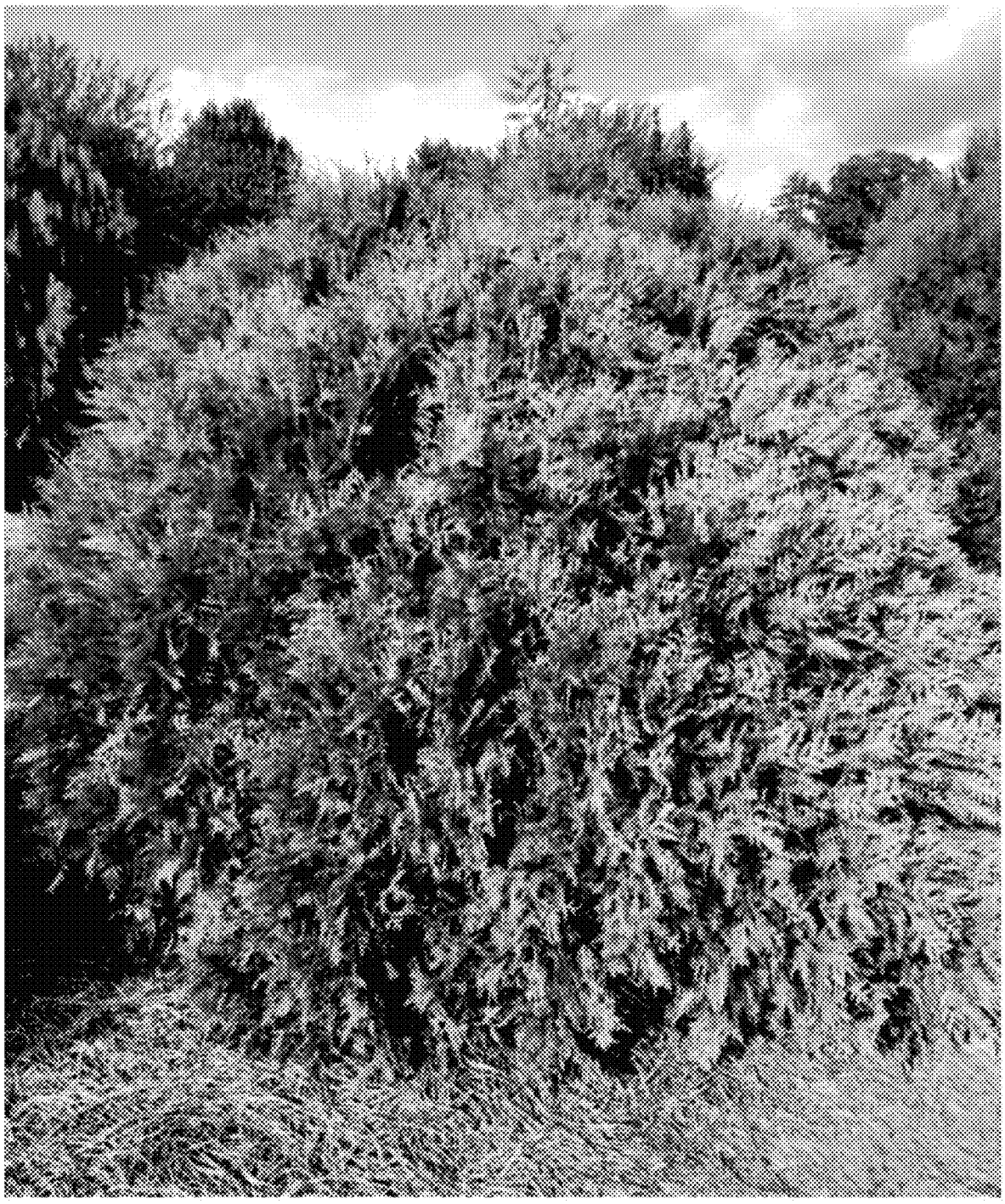

Botanical designation: *Thuja occidentalis.*
Cultivar denomination 'RutThu4'.

BACKGROUND OF THE INVENTION

The present invention relates to a new and distinct cultivar of *Thuja*, botanically know as *Thuja occidentalis*, and hereinafter referred to by the cultivar name 'RutThu4'.

The new *Thuja* cultivar 'RutThu4' is a product of open pollination of *Thuja occidentalis* 'Filiformis' (unpatented). The open-pollinated seeds were obtained in 2010 from American Conifer Society. Seedlings were planted in Watkinsville in 2014 The new cultivar 'RutThu4' was selected for its compact, globose growth form, faster growth rate than *Thuja occidentalis* 'Little Giant', disease resistance in USDA Zone 8a, heat tolerance, and cold hardiness to about −34° F. in trials conducted in Minnesota.

Asexual reproduction of the new *Thuja* 'RutThu4' using hardwood cuttings has been continued in Watkinsville, Ga. since 2015. Observations of the resulting progeny have shown that the unique features of this new *Thuja* 'RutThu4' are stable and reproduced true to type in successive generations. The new 'RutThu4' has also been grown in Minnesota.

SUMMARY OF THE INVENTION

The new *Thuja* cultivar 'RutThu4' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Thuja* cultivar named 'RutThu4'. In combination, these traits set 'RutThu4' apart from all other existing varieties of *Thuja* known to the inventors.

1. compact, globose growth form;
2. faster growth rate than *Thuja occidentalis* 'Little Giant';
3. resistance to diseases common to other *Thuja* cultivars in USDA zone 8a, specifically *Passalora* spp.;
4. heat tolerance
5. cold hardiness to about −34° F. in trials conducted in Minnesota.

Plants of the 'RutThu4' can be compared to similar cultivar *Thuja occidentalis* 'Little Giant' (unpatented) differs from 'Little Giant' in that 'RutThu4' has a similar rounded shape as 'Little Giant' while being larger (both taller and wider) than 'Little Giant' (which is about 36"×48", as compared to about 58"×80" for 'RutThu4'). Male parent plant is not conclusively known, so comparison data is not available. The new *Thuja* 'RutThu4' can also be compared to *Thuja occidentalis* cultivars 'Filiformis' (female parent) in that 'RutThu4' has foliage typical of the species, unlike 'Filiformis'.

BRIEF DESCRIPTION OF THE PHOTOGRAPHS

The accompanying, colored photographic illustrations show the overall appearance and distinct characteristics of the new cultivar *Thuja* 'RutThu4' showing the colors as true as possible. Colors in the photographs may differ slightly from the color values cited in the detailed botanical description. The photographs were taken around June, 2021 of plants grown outdoors in Watkinsville, Ga.

The photograph labeled FIG. 1 depicts a side view of a typical 7-year-old 'RutThu4' plant showing the rounded, compact globose form and features.

Figure 2:
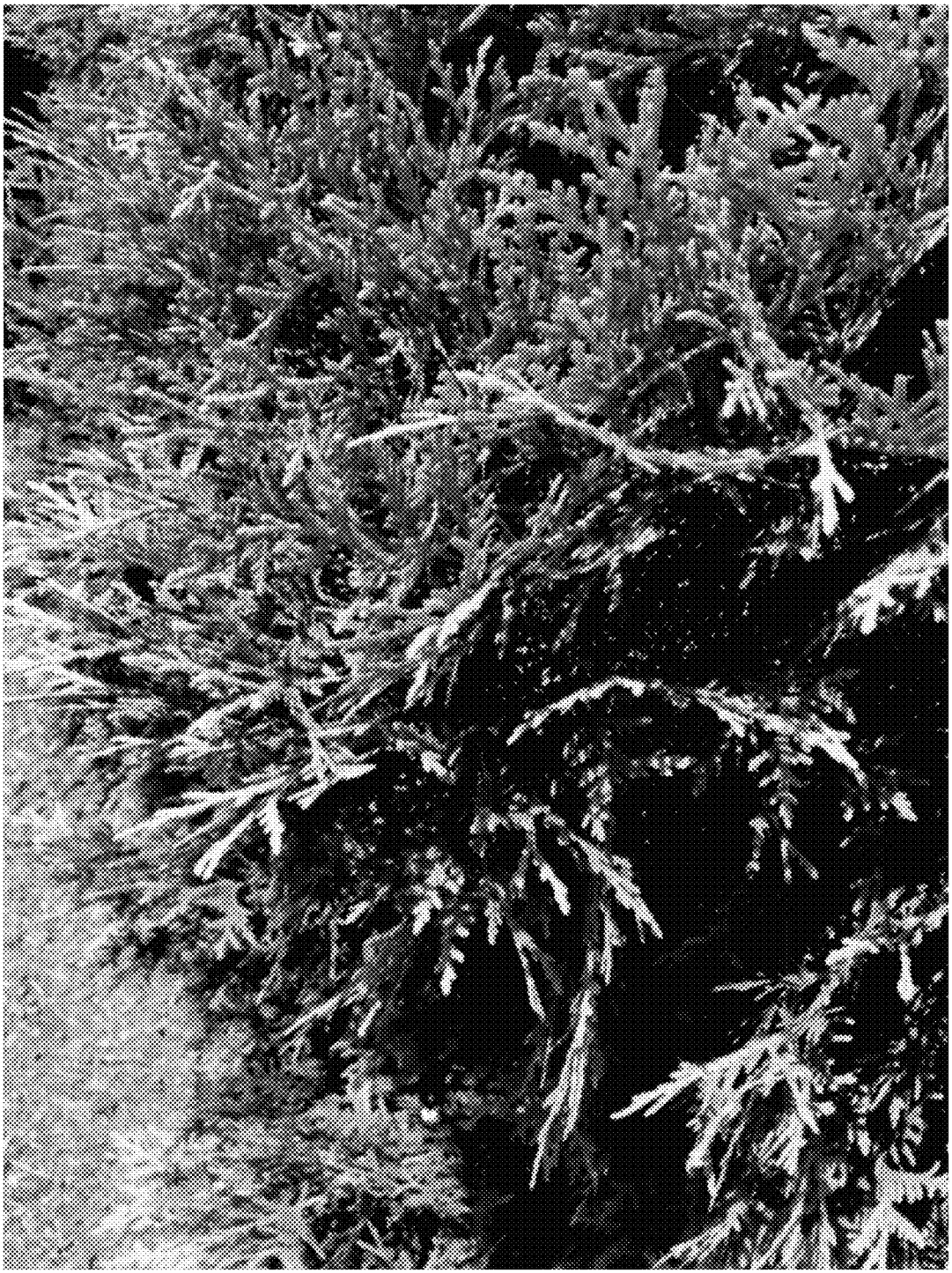

The photograph labeled FIG. 2 depicts a close-up view of the branches and needles of a typical 7-year-old 'RutThu4' plant.

DETAILED BOTANICAL DESCRIPTION

The following traits have been consistently observed in the original plants of the new varieties and in asexually propagated progeny grown in Watkinsville, Ga., (and some in Minnesota) and, to the best knowledge of the inventors, their combination forms the unique characteristics of the new variety 'RutThu4'.

Throughout this specification, color names beginning with a small letter signify that the name of that color, as used in common speech, is aptly descriptive. Color names beginning with a capital letter designate values based upon The R.H.S. Colour Chart, 5th edition published by The Royal Horticultural Society, London, England in 2007, except where general terms of ordinary dictionary significance are used The aforementioned photographs and following observations, measurements, and values describe plants of the *Thuja* cultivar named 'RutThu4'. Data were collected from a horticulture farm in Watkinsville, Ga. from 6-year-old plants. The average low temperatures ranged from about 20° F. to 30° F. in the winter and about 90° F. to 100° F. in summer.

Botanical classification: *Thuja occidentalis* 'RutThu4'.

Commercial classification: Ornamental conifer.

Parentage: Open pollination of *Thuja occidentalis* 'Filiformis' by unknown pollen parents.

Growth and propagation:

*Propagation type*.—Terminal or sub-terminal hardwood cuttings.

*Growth rate*.—Slow to moderate.

*Root description*.—Typically about 2-5 roots arising from the base of the cuttings.

*Rooting habit*.—Good.

Plant description:

*Habit*.—Of 6-year-old plant in field — compact round/globose, about symmetrical.

*Usage*.—Various uses, including landscaping, ornamental, container, border, hedge, and mass planting.

*Vigor*.—Moderate.

*Size of 6-year-old plant*.—A. Height: from soil level to top of plant, about 58 inches. B. Width: about 80 inches. C. Ratio: about 0.73.

*Branch/stem (terminal tuft)*.—A. Quantity: numerous. B. Length: about 13-14.5 cm. C. Base Diameter: about 2-3 mm at about 15 cm from tip. D. Branch angle: about 65° from center. E: Odor (of bruised stem): moderate evergreen scent. F. Internode length: about 1-1.5 mm (about 5 internodes per sample). G: Color (R.H.S.): Greyed-orange 166A. H: Strength of lateral branches: moderate. I: Pubescence: has scale that peel off but do not shed. J: Shape: round.

*Leaf*.—A. Leaf type: needles. B. Mature size (L×W): about 5-9 cm×about 2-3 cm. C. Arrangement on stem: alternate. D. Aspect: upright. E. Color (R.H.S.): summer — upper and lower, Green 137B, tips have tinge of Yellow-Green 144C. winter — upper is Greyed-orange 165A; lower is Greyed-Orange 166D. F. Leaf Number: average of about 8 per cm/stem. G. Apex: acute. H. Base: cuneate. I. Margin: entire. J. Shape: linear with scale-like structure, no lobes present. K. Pubescence: none. L. Venation: none. M. Texture: smooth, glossy. O. Odor when crushed: light evergreen scent.

*Coning production*.—None observed.

*Seed*.—None observed.

Weather/temperature tolerance: Plants of the new *Thuja* have been observed to grow in USDA Zone 8a, with heat tolerance, and have a USDA Zone range 3-8. 'RutThu4' has also been cold hardy to about −34° F. in trials conducted in Minnesota.

Disease/pest resistance: To date, plants of the new *Thuja* have been observed to have disease resistance *Passelora* spp. in USDA Zone 8a when grown under standard conditions.

It is claimed:

1. A new and distinct cultivar of the *Thuja* plant named 'RutThu4' as illustrated and described herein.

* * * * *